US00PP12230P2

(12) United States Plant Patent
Lemon

(10) Patent No.: US PP12,230 P2
(45) Date of Patent: Nov. 27, 2001

(54) VARIETY OF GERANIUM PLANT NAMED 'PATRIOT SALMON'

(75) Inventor: David Lemon, Santa Barbara, CA (US)

(73) Assignee: Ogleve, Ltd., Connellsville, PA (US)

( * ) Notice: Subject to any disclaimer, the term of this patent is extended or adjusted under 35 U.S.C. 154(b) by 0 days.

(21) Appl. No.: 09/715,314

(22) Filed: Nov. 17, 2000

(51) Int. Cl.[7] ..... A01H 5/00

(52) U.S. Cl. ..... Plt./327

(58) Field of Search ..... Plt./327, 325, 328

*Primary Examiner*—Amy J. Nelson
*Assistant Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with bright striking shades of coral, pink, and salmon colored flowers above medium green foliage with prominent zonation.

1 Drawing Sheet

BACKGROUND OF THE INVENTION

The present invention comprises a new and distinct cultivar of *Pelargonium×hortorum* known by the varietal name 'Patriot Salmon' (Oglevee No. 5048, Breeder No. 4DG791). The new variety was discovered in a selected breeding program in Lompoc, Calif. The new variety is a selection from the cross of 'Eclipse Light Salmon', the female parent, and 'Salmon Satisfaction', the male parent (U.S. Plant Pat. No. 7,926 and 7,610, respectively). The new variety was first asexually reproduced by cuttings at Oglevee, Ltd. in Connellsville, Pa. The new variety has been trial and field tested at Connelsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of six weeks from a rooted cutting to flowering in a 10 cm pot. The response time was determined on plants grown in soilless media employing constant fertilizer 200–250 parts per million of nitrogen and potassium in full light. Plants of 'Patriot Salmon' differ from the plants of the parental cultivars primarily in flower color.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Connellsville, Pa. The color readings were taken indoors under 200–220 foot candles of fluorescent cool white light. Color references are primarily to The R.H.S. Colour Chart of The Royal Horticultural Society of London. Plants described were about 6 weeks old from a rooted cutting.

PLANT

Classification:
- *Botanical.*—*Pelargonium×hortorum.*
- *Commercial.*—*Zonal geranium.*

Form: Medium mound.
Height: 13.0–17.0 cm from soil to top of foliage.
Growth: Upright, free basal branching.
Strength: Does not require artificial support.
Foliage: Prominent zonation; stalked leaf attachment.
Rooting time: Roots visible to the outside of an artificial dirt plug in 10–14 days.
Leaves:
- *Size.*—Length: 5.5–6.5 cm. Width: 6.7–8.0 cm.
- *Shape.*—Reniform; cordate base.
- *Margin.*—Crenate.
- *Texture.*—Pubescent.
- *Color.*—Upper surface: Green-Group 137C. Lower surface: Green Group 138B. Zonation: Yellow-Green Group 147A.
- *Ribs and veins.*—Venation: Palmate.
- *Color.*—Yellow-Green Group 145B.

Petioles:
- *Color.*—*Yellow-Green Group* 144A.
- *Length.*—4.6–6.5 cm.

Stem:
- *Color.*—Yellow-Green Group 144A.
- *Internode length.*—2.5–3.5 cm.

THE BUD

Shape just prior to anthesis:
- *Overall.*—Elliptical cluster.
- *Individual bud.*—Elliptical.

Size:
- *Overall.*—4.0–4.3 cm across when just showing color. 2.0 cm across when showing no color.
- *Individual bud.*—0.7–1.2 cm long; 0.6–0.8 cm wide when just showing color.

Number of buds per cluster: 23–32.

INFLORESCENCE

Blooming habit: Continuous; free and early flowering.
- *Size.*—11.0–12.5 cm.
- *Borne.*—Flower on umbel; umbel pedicel; pedicel on peduncle; 7.5–10.5 cm above foliage.

Flowers:
- *Form.*—Flat to slightly cupped.
- *Number of flowers per umbel.*—18–25.

*Size.*—Length: 2.0–3.0 cm. Width: 4.5–5.0 cm.

*Petals.*—Color: Upper surface: There is a wide range of colors in each bloom, and in each individual petal. On the younger blooms: Generally, outer edge is Red Group 48C, moving to Red Groups 41C–41D. Some petals fade to Red Group 39D. Very base of petal is white. Veining of various degrees of colors is present. These colors range from the darkest of Red Group 42D and Red Group 52D to lighter colors of Red Group 39C. As the bloom ages the color tends to deepen and take on a pinker tone: Outer edge, Red Group 52A shading to Red Group 48B in middle. This color then fades to Red Group 52D toward the base, and white at the very base. Veining is of the same colors as younger blooms. Lower surface: Various degrees of colors present. Overall colors are: younger blooms — Red Group 49B; older blooms — Red Group 52D. Shape: Obovate. Size: Length: 2.5–3 cm. Width: 1.5–2 cm. Margin: Entire. Number per flower: 6–8.

Texture and appearance: Smooth, velvety, slighty reflective.

Tonality from a distance: Flowers of deep salmon above a mound of medium green foliage with a striking zone present.

Petaloids:

Quantity.—2–4.

*Shape.*—Irregular; some twisted, some tubular, some with pollen attached.

*Color.*—Same as petals.

Pedicel:

*Length.*—2.3–3 cm.

*Color.*—Near flower is Red Group 53A fading to Greyed-Orange Group 174C.

Peduncle:

*Length.*—16.5–19 cm.

*Color.*—Yellow-Green Group 144A.

Disease/pest resistance: No susceptibility to diseases or pests has been noted to date.

Lasting quality: Individual umbels will last from 7–14 days depending on weather conditions. Overall blooming habit is continuous throughout the growing season.

REPRODUCITVE ORGANS

Stamens:

Anthers.—2 mm long.

*Filaments.*—Length: 0.5–0.7 cm. Color: White with coral colored tips. Pollen: Golden brown.

Pistils:

*Number.*—One.

*Length.*—0.7–1.0 cm.

*Stigma.*— Number: One; five to six parted. Color: Red-Purple Group 59C.

*Style.*— Length: 0.4–0.5 cm. Color: Red-Purple Group 59C.

Ovaries:

*Completeness.*—Superior.

*Pubescence.*—Very pubescent.

*Length.*—0.5–0.6 cm.

*Width.*—0.4–0.5 cm.

*Color.*—Pale green.

Fruit: None observed.

GENERAL CHARACTERISTICS

1. 'Patriot Salmon' exhibits a more controlled plant habit than the current variety 'Patriot Salmon Blush' (U.S. Plant Pat. No. 10,471). The medium green foliage has a distinct zone and the flowers exist bright striking shades of coral, pink, and salmon flowers.
2. Cutting amount and rooting speeds are comparable to 'Patriot Salmon Blush'.
3. Indoor finishing performance is very good. Flowering will occur six week after potting. The more controlled habit allows for tighter spacing on the bench resulting in more crops sold.
4. Outdoor performance has been trialed during the growing seasons of 1995, 1996, 1997, 1998, 1999, and 2000 with very good results regardless of the weather conditions.

I claim:

1. A new and distinct variety of geranium plant substantially as shown and described.

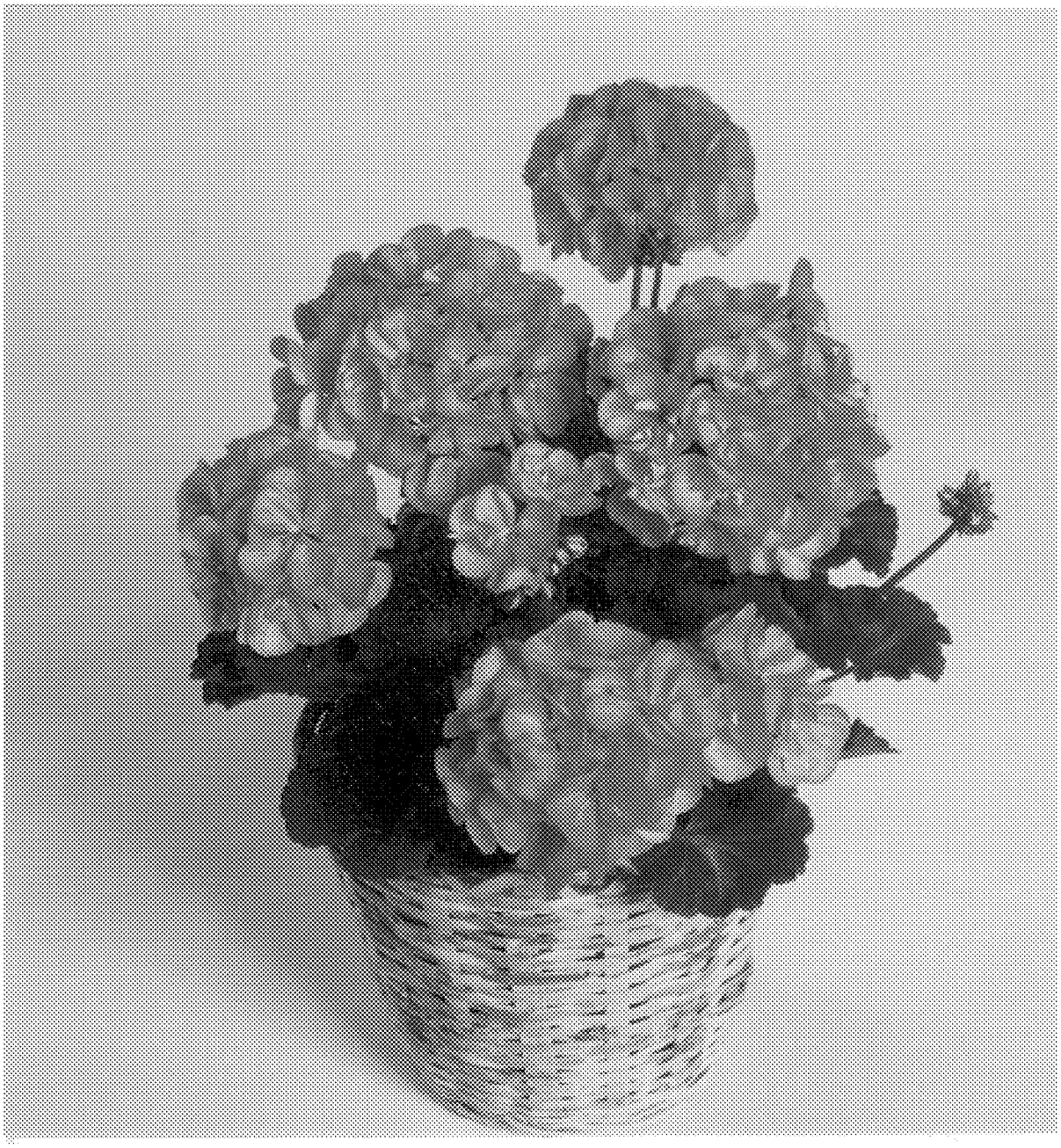

* * * * *